(12) United States Patent
Roundhill et al.

(10) Patent No.: US 11,684,343 B2
(45) Date of Patent: Jun. 27, 2023

(54) TRANSLATION OF ULTRASOUND ARRAY RESPONSIVE TO ANATOMICAL ORIENTATION

(71) Applicant: KONINKLIJKE PHILIPS N.V., Eindhoven (NL)

(72) Inventors: David Nigel Roundhill, Woodinville, WA (US); Jeffrey Scott Hart, Port Royal, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 951 days.

(21) Appl. No.: 15/319,956

(22) PCT Filed: Jun. 16, 2015

(86) PCT No.: PCT/IB2015/054528
§ 371 (c)(1),
(2) Date: Dec. 19, 2016

(87) PCT Pub. No.: WO2016/001784
PCT Pub. Date: Jan. 7, 2016

(65) Prior Publication Data
US 2017/0128045 A1 May 11, 2017

Related U.S. Application Data

(60) Provisional application No. 62/018,706, filed on Jun. 30, 2014.

(51) Int. Cl.
*A61B 8/00* (2006.01)
*A61B 8/08* (2006.01)
(Continued)

(52) U.S. Cl.
CPC .......... *A61B 8/4461* (2013.01); *A61B 8/0866* (2013.01); *A61B 8/145* (2013.01);
(Continued)

(58) Field of Classification Search
CPC ..... A61B 8/4461; A61B 8/0866; A61B 8/145; A61B 8/4218; A61B 8/4494; A61B 8/46;
(Continued)

(56) References Cited

U.S. PATENT DOCUMENTS 4,381,787 A * 5/1983 Hottinger ............. G10K 11/357
600/443
6,780,153 B2 * 8/2004 Angelsen ................. A61B 8/00
600/444
(Continued)

FOREIGN PATENT DOCUMENTS

WO 2013088326 A2 6/2013
WO WO-2013088326 A2 * 6/2013 ........... A61B 8/5215
WO 2014080319 A1 5/2014

OTHER PUBLICATIONS

Fenster et al., "Three-dimensional ultrasound scanning", Interface Focus (2011), vol. 1, published online Jun. 1, 2011, pp. 503-519.
(Continued)

Primary Examiner — Sean D Mattson

(57) ABSTRACT

A medical imaging system configured to analyze an acquired image to determine the imaging plane and orientation of the image. The medical imaging system may be further configured to determine a location of an aperture to acquire a key anatomical view and transmit instructions to a controller to move the aperture to the location. A sonographer may not need to move the ultrasound probe for the medical imaging system to move the aperture to the location. An ultrasound probe may include a transducer array that may have one or more degrees of freedom of movement within the probe. The transducer array may be translated by one or more motors that receive instructions from the controller to position the aperture.

22 Claims, 4 Drawing Sheets

(51) Int. Cl.
- *G01S 15/89* (2006.01)
- *G01S 7/52* (2006.01)
- *G10K 11/35* (2006.01)
- *A61B 8/14* (2006.01)

(52) U.S. Cl.
CPC .......... *A61B 8/4218* (2013.01); *A61B 8/4494* (2013.01); *A61B 8/46* (2013.01); *A61B 8/5269* (2013.01); *A61B 8/54* (2013.01); *A61B 8/585* (2013.01); *G01S 7/52079* (2013.01); *G01S 7/52098* (2013.01); *G01S 15/8915* (2013.01); *G01S 15/8925* (2013.01); *G01S 15/8936* (2013.01); *G01S 15/8993* (2013.01); *G10K 11/352* (2013.01); *G01S 7/5208* (2013.01)

(58) Field of Classification Search
CPC ......... A61B 8/5269; A61B 8/54; A61B 8/585; G01S 7/52079; G01S 7/52098; G01S 7/5208; G01S 15/8915; G01S 15/8925; G01S 15/8936; G01S 15/8993; G01K 11/352

See application file for complete search history.

(56) References Cited

U.S. PATENT DOCUMENTS

| | | | |
|---|---|---|---|
| 8,206,307 | B2 | 6/2012 | Barnard et al. |
| 8,235,909 | B2 | 8/2012 | Barthe et al. |
| 11,540,718 | B2* | 1/2023 | Waechter-Stehle .... A61B 8/461 |
| 2002/0133078 | A1* | 9/2002 | Jordfald ................. A61B 8/12 |
| | | | 600/462 |
| 2002/0173721 | A1* | 11/2002 | Grunwald ................. A61B 8/00 |
| | | | 600/437 |
| 2004/0254466 | A1 | 12/2004 | Boner et al. |
| 2005/0124880 | A1* | 6/2005 | Shinomura ............... A61B 8/13 |
| | | | 600/437 |
| 2006/0184031 | A1* | 8/2006 | Ichioka ................. A61B 8/0866 |
| | | | 600/447 |
| 2007/0239020 | A1 | 10/2007 | Iinuma |
| 2009/0036780 | A1 | 2/2009 | Abraham |
| 2009/0306509 | A1* | 12/2009 | Pedersen ............. G01S 15/8936 |
| | | | 600/446 |
| 2010/0168577 | A1* | 7/2010 | Vezina ................. A61B 8/4236 |
| | | | 600/443 |
| 2010/0262008 | A1* | 10/2010 | Roundhill ............... A61B 8/00 |
| | | | 600/453 |
| 2010/0305441 | A1* | 12/2010 | Lin .......................... A61B 8/00 |
| | | | 600/443 |
| 2011/0172532 | A1* | 7/2011 | Yoo ........................ G01S 7/5205 |
| | | | 600/443 |
| 2011/0246129 | A1* | 10/2011 | Ishikawa ............... A61B 8/4245 |
| | | | 702/150 |
| 2012/0065510 | A1* | 3/2012 | Snare ....................... A61B 8/14 |
| | | | 600/443 |
| 2013/0053681 | A1 | 2/2013 | Endo et al. |
| 2014/0213903 | A1* | 7/2014 | Seo ........................ A61B 34/32 |
| | | | 600/439 |

OTHER PUBLICATIONS

Housden, et al., "Rotational motion in sensorless freehand three-dimensional ultrasound", Ultrasonics, Sep. 2008, vol. 48, Issue 5, pp. 412-422 (Abstract).

* cited by examiner

TRANSLATION OF ULTRASOUND ARRAY RESPONSIVE TO ANATOMICAL ORIENTATION

This application is the U.S. National Phase application under 35 U.S.C. § 371 of International Application No. PCT/IB2015/054528, filed on Jun. 16, 2015, which claims the benefit of Provisional Application Ser. No. 62/018,706, filed Jun. 30, 2014. These applications are hereby incorporated by reference herein.

BACKGROUND

Fetal images are generally acquired multiple times during gestation to ensure that the fetus is developing normally. Key anatomical views that are defined by standard practice guidelines are acquired. Most fetal images are acquired by ultrasound imaging systems operated by a trained sonographer. To obtain the key anatomical views, careful manipulation of an ultrasound transducer is required to place the imaging plane of the transducer in precise alignment with the fetal anatomy. This may be difficult even for a skilled practitioner due to the wide variety of fetal lies, that is, the position and articulation of the fetus within the uterus. The fetus may also move during the exam.

Three-dimensional (3D) ultrasound may be used to reduce the need for fine movements of the transducer. A volume may be acquired using a matrix array transducer or by mechanically sweeping a two-dimensional array transducer through a volume. The sonographer may generate multiplanar reconstruction views (MPR) from the acquired 3D volume. However, the MPR view may have significantly compromised image resolution due to the variable resolution of the ultrasound acoustic aperture. Matrix transducers may mitigate the variable resolution by having aperture dimensions similar in both the elevation and azimuthal planes. Such matrix transducers are costly and technically challenging to manufacture.

If key anatomical views are unable to be acquired or the images acquired of insufficient resolution for a reviewing physician to make a diagnosis, a pregnant subject may be requested to return for additional imaging exams. In addition to increased medical costs, this may be inconvenient for the subject due to time or travel constraints. It may also cause undo anxiety to the subject as she may believe additional imaging exams are necessary because the reviewing physician found a reason for concern in the previously acquired images of the fetus.

SUMMARY OF THE INVENTION

According to one illustrative embodiment of the invention disclosed, a medical imaging system may be configured to acquire a first image, determine an image plane and an orientation of the first image, determine sufficiency of the first image, calculate a position for an aperture to obtain a second image in a scan plane of the aperture, and move the aperture to the position to acquire the second image. The medical imaging system may be further configured to alert a user if the aperture cannot be moved to the position. The medical imaging system may be further configured to acquire the second image and determine the sufficiency of the second image. The medical imaging system may be further configured to alert a user to sufficiency of at least one of the first image and the second image. The aperture may be moved by translating an ultrasound transducer probe with a motor. The aperture may be moved by beamforming an ultrasound transducer array. The image plane and the orientation of the first image may be determined at least in part by an articulated rigid body transformation model. The image plane and orientation of the first image may be determined at least in part by a deformable template model. Sufficiency of the first image may be determined at least in part by a resolution of the first image. Sufficiency of the first image may be determined at least in part by the first image containing an entire key anatomical view. Sufficiency of the first image may be determined, at least in part, by the first image being acquired in the scan plane of the aperture.

According to another illustrative embodiment of the invention disclosed, a method may include receiving an acquired image at a medical imaging system; analyzing the acquired image with a processor of the medical imaging system; calculating a position of an aperture to acquire a desired image in a scan plane of the aperture with the processor; calculating a movement of an ultrasound array to move the aperture to the position with the processor; transmitting instructions for the movement to a controller from the processor. The method may further include receiving a new acquired image at the medical imaging system. The instructions may be instructions for a motor. The instructions may be instructions for beamforming with an ultrasound transducer. Analyzing the acquired image may include fitting the acquired image to an anatomical model to determine an imaging plane and an orientation of the acquired image. Analyzing the acquired image may include determining a resolution of the acquired image. The method may further include transmitting instructions for the movement to a user from the processor. The desired image may include an entire key anatomical view. The desired image may have a resolution adequate for diagnostic purposes.

According to a further illustrative embodiment of the invention disclosed, an ultrasound probe may include an articulated chassis, a transducer array mounted to the chassis, a dome over the transducer array, a first motor coupled to the chassis configured to move the transducer array about a first axis of rotation, and a second motor coupled to the chassis configured to move the transducer array about a second axis of rotation. The first motor and the second motor may be configured to move the transducer array about the first axis and the second axis simultaneously. The first motor and the second motor may be configured to be coupled to a motor controller.

DETAILED DESCRIPTION

Figure 1:
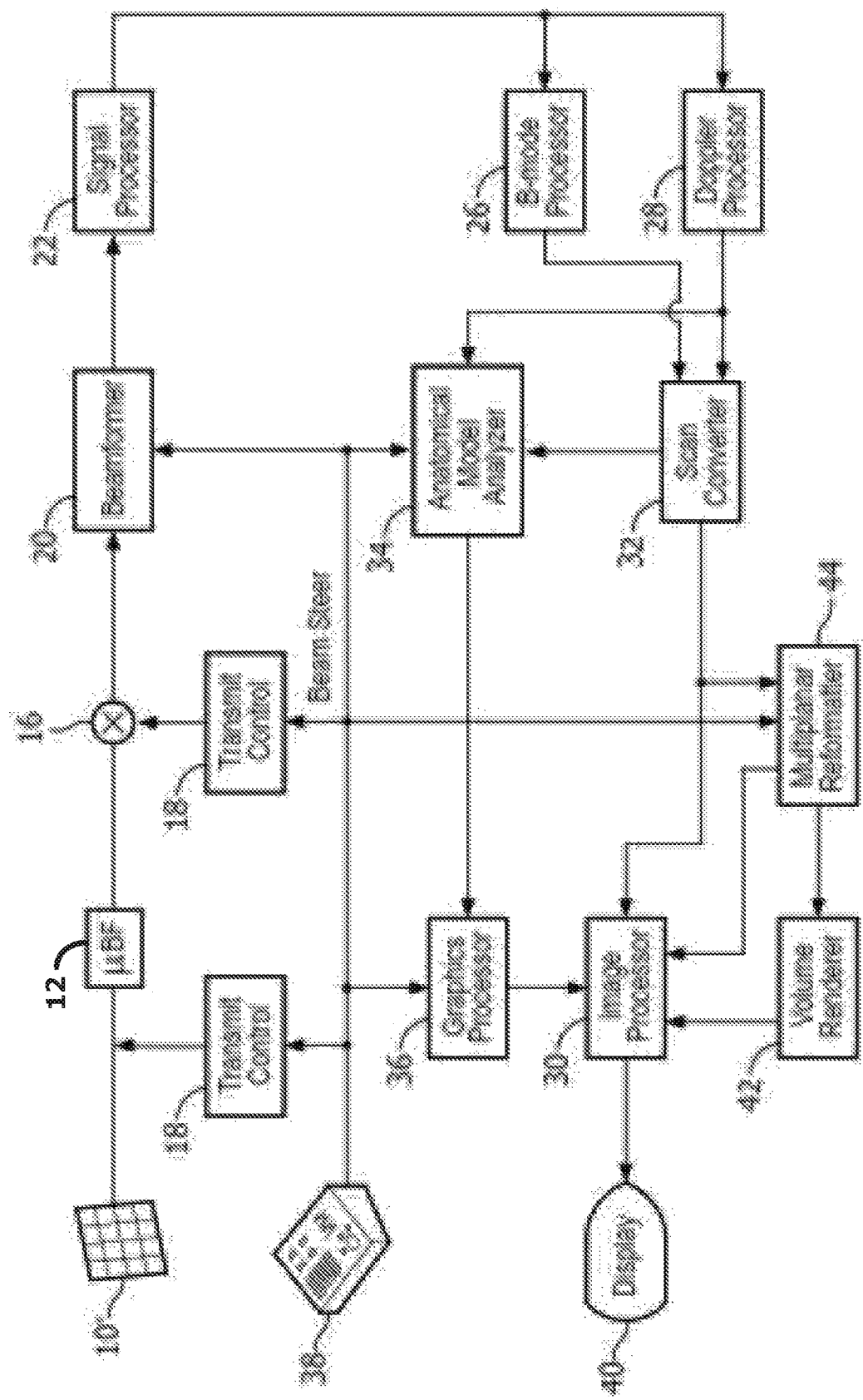
FIG. 1 is a schematic view of an embodiment of an ultrasound imaging system according to an illustrative embodiment of the invention.

In the following detailed description, for purposes of explanation and not limitation, illustrative embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the illustrative embodiments. Such methods and apparatus are within the scope of the present teachings.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

The anatomically intelligent systems and methods of the present invention provide, e.g., for quickly and accurately generating ultrasound images (e.g., 2D or 3D ultrasound images, such as a B-mode image or 3D volume image, respectively) having optimal characteristics, such as optimal image resolution and/or optimal orientation for viewing of anatomical structures in a patient. In some aspects, for example, a sonographer may begin scanning a patient, and an ultrasound system coupled with a smart probe of the present invention can automatically orient the ultrasound beam to acquire an optimal image for the given position of the probe. The automatic movement and orientation of the ultrasound beam can be accomplished in a variety of ways. In certain aspects, for example, orientation of the ultrasound beam can include mechanically or electronically moving the ultrasound beam in space, moving the position of the transducer probe with a robotic arm or other mechanical or human-driven device, or a combination thereof. The anatomically intelligent features of the present invention, in particular, provide a variety of approaches that will save time and effort for sonographers, especially those sonographers that may be less skilled. Moreover, the systems and methods of the present invention remove complexities in collected optimal images, especially in scenarios like fetal imaging that require quick assessment and acquisition.

As provided herein, the present invention can include a system, application, and/or method for automatically translating an aperture of an ultrasound array so as to acquire a key anatomical view in the scan plane of the aperture. For example, an imaging plane aligned with an aperture of an ultrasound transducer array may have higher resolution than imaging planes outside the imaging plane aligned with the aperture. The key anatomical view acquired in the scan plane of the aperture, however, may have sufficient resolution to be useful for diagnostic purposes. Accordingly, required manual movement of the ultrasound probe by a sonographer and image acquisition time may be reduced. Requiring subjects to return for additional imaging exams due to the acquisition of poor quality images may also be reduced.

As will be described further herein, the present invention includes ultrasound imaging systems and transducer probes that can, e.g., include hardware and software configurations designed to operate automatically and with minimal input from a user. A variety of transducer probes can be used, for example, to orient an ultrasound beam in response to imaged anatomical features and/or other image characteristics. Referring to FIG. 1, an ultrasound imaging system constructed in accordance with the principles of the present invention is shown in block diagram form. In the ultrasonic diagnostic imaging system of FIG. 1, a transducer array 10' is provided in an ultrasound probe for transmitting ultrasonic waves and receiving echo information. The transducer array 10' may be, for example, a two dimensional array of transducer elements capable of scanning in three dimensions (e.g., in both elevation and azimuth dimensions) about a location for 3D imaging. The aperture of the two dimensional array may have freedom of movement in one or more dimensions by utilizing beamforming methods. In certain embodiments, the two dimensional transducer array may also be translated by motors as depicted, e.g., in FIG. 3. In some embodiments, the transducer array may be a 1D, 1.25D, or 1.5D array, and the ultrasound probe may contain motors (not shown in FIG. 1) for mechanically moving (e.g., translating and/or rotating) the transducer array 10' within the ultrasound probe to alter the position of the imaging aperture of the probe. The motors may be coupled to a motor controller, described in more detail below, which is configured to operate the motors in the probe. The transducer array 10' may have freedom of movement around one or more axes of rotation.

In certain embodiments, the present invention includes transducer probes that, in combination with an ultrasound system, are anatomically intelligent and configured to move an array in space so as to, e.g., optimize anatomical views and/or image characteristics in real-time and with minimal user input. In some aspects, the present invention includes ultrasound probes that can move the ultrasound beam in virtually any desired orientation. For example, the ultrasound beam can be moved in at least two degrees of freedom (e.g., translation and rotation). The ultrasound beam can be translated mechanically and/or electronically via beamforming.

Figure 2:
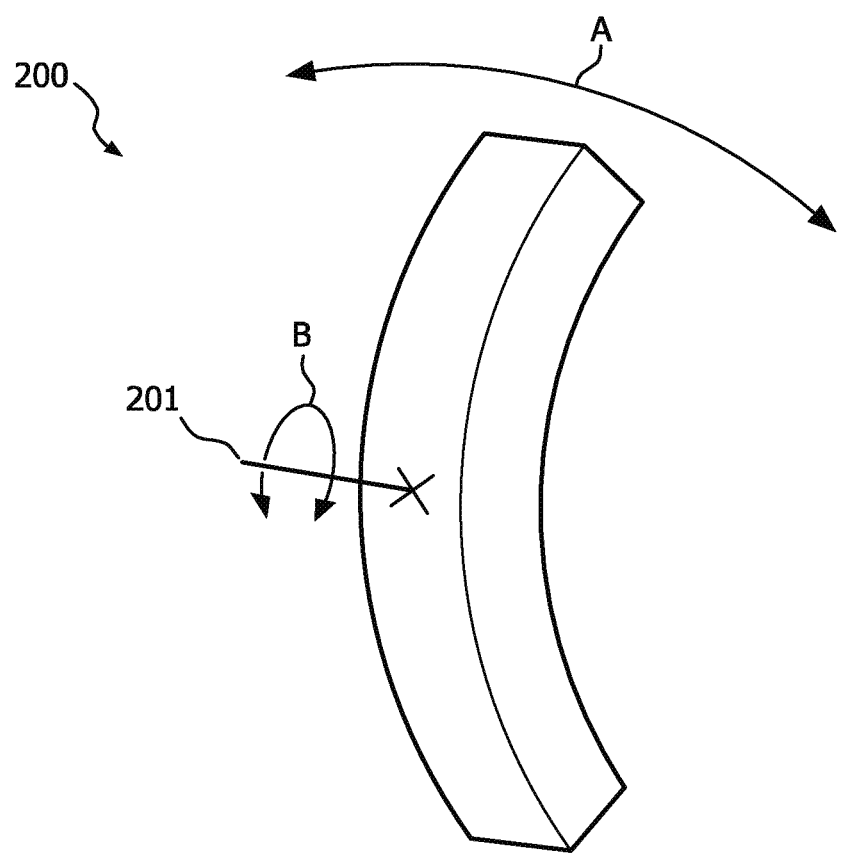
FIG. 2 is a schematic view of an ultrasound transducer array according to an illustrative embodiment of the invention.

In certain aspects, an ultrasound probe of the present invention may include an articulated chassis, a transducer array mounted to the chassis, a dome over the transducer array, a first motor coupled to the chassis configured to move the transducer array about a first axis of rotation, and a second motor coupled to the chassis configured to move the transducer array about a second axis of rotation. The first motor and the second motor may be configured to move the transducer array about the first axis and the second axis simultaneously. The first motor and the second motor may be configured to be coupled to a motor controller. FIG. 2 provides an example of a transducer array 200 which may be used as transducer array 10' in FIG. 1 is shown. The transducer array 200 may be moved in multiple dimensions. A first degree of freedom illustrated by arrow A, wherein the transducer array 200 may be translated about an axis vertical and in line with the page. That is, the transducer array 200 may be translated into and out of the page in relation to the reader as illustrated by arrow A. The transducer array 200 has a second degree of freedom around an axis of rotation about a center point 201 illustrated by arrow B. An ultrasound probe having fewer or more axes of rotation and/or degrees of freedom may be used as well. Moving the position of the transducer array 200 along a direction of arrows A and/or B within the probe may change the location of the aperture, which may allow for the acquisition of a desired image at a higher resolution without requiring the sonographer to change the location of the probe itself.

Figure 3:
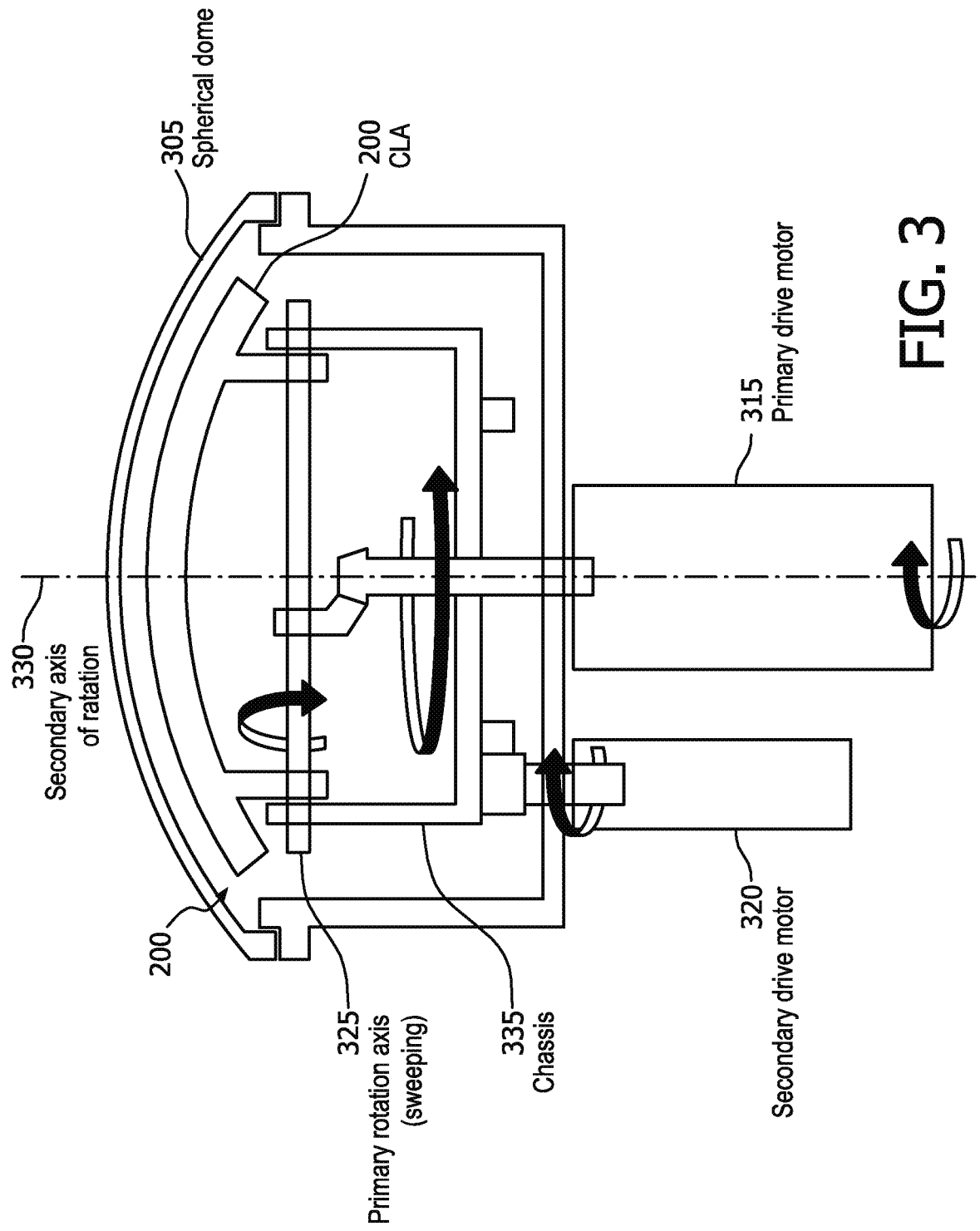
FIG. 3 is a schematic view of an ultrasound probe according to an illustrative embodiment of the invention.

An example embodiment of an ultrasound probe 300, which may be used following the principles of the invention, is shown in FIG. 3. The probe 300 may contain the translatable transducer array 200 shown in FIG. 2. The probe 300 has a spherical dome 305 which may enclose the ultrasound transducer array 200. The dome may comprise a material that improves acoustical coupling between the probe and the subject. The transducer array 200 may be coupled to an articulated chassis 335. The chassis 335 may allow the transducer array 200 to move freely around axes of rotation 325, 330. The chassis 335 may be coupled to motors 315, 320 that move the chassis 335 around axis 325 and axis 330, respectively. The motors 315, 320 may be coupled to the motor controller. The motors 315, 320 may translate the transducer array 200 to a desired position according to instructions received from the motor controller. The motors 315, 320 may operate in concert such that the transducer array 200 is moved across both axes of rotation simultaneously. The probe illustrated in FIG. 3 is only one example of an ultrasound probe that may be used in accordance with principles of the invention, and other ultrasound probes with different transducer, motor, and chassis designs may be used without departing from the scope of the invention. An example of an alternative probe design that may be used in accordance with the principles of the invention is described in U.S. Pat. No. 8,475,384 "Three Dimensional Imaging Ultrasound Probe," issued on Jul. 2, 2013.

Referring back to FIG. 1, the transducer arrays described herein may be further coupled to a microbeamformer 12 in the probe which controls transmission and reception of signals by the array elements. The microbeamformer is coupled by the probe cable to a transmit/receive (T/R) switch 16 which switches between transmission and reception and protects the main beamformer 20 from high energy transmit signals. The transmission of ultrasonic beams from the transducer array 10' under control of the microbeamformer 12 is directed by the transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view. The partially beamformed signals produced by the microbeamformer 12 are coupled to a main beamformer 20 where partially beamformed signals from the individual patches of elements are combined into a fully beamformed signal. Beamforming may also be used in some embodiments to alter the location of the imaging aperture to acquire a desired image. Beamforming may be used in conjunction with motors to move the transducer array 10' to alter the location of the aperture.

The beamformed signals are coupled to a signal processor 22. The signal processor 22 can process the received echo signals in various ways, such as bandpass filtering, decimation, I and Q component separation, and harmonic signal separation. The signal processor may also perform additional signal enhancement such as speckle reduction, signal compounding, and noise elimination. The processed signals are coupled to a B mode processor 26 and a Doppler processor 28. The B mode processor 26 employs amplitude detection for the imaging of structures in the body such as the heart or a tumor. The Doppler processor 28 processes temporally distinct signals from tissue and blood flow for the detection of the motion of substances such as the flow of blood cells in the image field. The structural and motion signals produced by the B mode and Doppler processors are coupled to a scan converter 32 and a multiplanar reformatter 44. The scan converter 32 arranges the echo signals in the spatial relationship from which they were received in a desired image format. For instance, the scan converter 32 may arrange the echo signal into a two dimensional (2D) sector-shaped format, or a pyramidal three dimensional (3D) image. The scan converter 32 can overlay a B mode structural image with colors corresponding to motion at points in the image field corresponding with their Doppler-estimated velocities to produce a color Doppler image which depicts the motion of tissue and blood flow in the image field. The multiplanar reformatter 44 can convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point, e.g., as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

A graphics processor 36 coupled to image processor 30, may generate graphic overlays for display with the ultrasound images on image display 40. These graphic overlays can contain standard identifying information such as patient name, date and time of the image, imaging parameters, and the like. For these purposes the graphics processor receives input from the user interface 38, such as a typed patient name. The user interface 38 is also coupled to the transmit controller 18 to control the generation of ultrasound signals from the transducer array 10' and hence the images produced by the transducer array and the ultrasound system. The user interface 38 is also coupled to the multiplanar reformatter 44 for selection and control of a display of multiple multiplanar reformatted (MPR) images.

The ultrasound systems of the present invention can be configured a variety of ways so that ultrasound images can be analyzed and used to determine how a transducer array can be oriented to automatically obtain a desired image without user instruction. In accordance with the principles of the present invention, an image (e.g., 2D or 3D ultrasound images) from the scan converter 32 are coupled to an anatomical model analyzer (AMA) 34. The AMA 34 may be implemented with computer accessible memory and a processor. The anatomical model analyzer 34 operates as described below to calculate the required orientation (e.g., translation and/or rotation) of the transducer array 10' to acquire a desired image at a scan plane aligned with the aperture of the transducer array 10'. The optimal orientation of the transducer may allow, e.g., the desired image to be acquired at a higher resolution than when acquired at scan planes not aligned with the aperture. In some embodiments, the anatomical model analyzer 34 may receive input from the user control panel 38, such as the type of exam performed and which standard view is being acquired. In other embodiments, the anatomical model analyzer 34 may automatically determine which standard view a user is attempting to acquire based at least in part on data received from the scan converter 32. A combination of both user instruction and automatic function may be used. Output data from the AMA 34 is coupled to the motor controller so as to orient the transducer array for image acquisition. The AMA 34 may provide, for example, instructions to the motor controller to translate the transducer array 10' to the appropriate position to move the position of the aperture to acquire the desired image from a scan plane aligned with the aperture. In other embodiments, the AMA 34 may provide instructions to the transmit control 18 instead of, or in addition to, the motor controller. The AMA 34 may provide instructions to the transmit control 18 for moving the aperture to a desired location via beamforming.

In some aspects, the present invention can also include hardware and software components, like the AMA, that can also manipulate and control positioning an orientation of the ultrasound transducer with a mechanical or human-driven device, such as a robotic arm. For example, the AMA can provide instructions to a robotic arm system, and optionally in conjunction with the transducer array, to move the transducer probe spatially to a position that generates an optimal image of a region of interest. As described further herein, the systems of the present invention may use algorithms to determine orientations of anatomical features being imaged. Through acquisition of one or more images (e.g., a 2D and/or 3D ultrasound image), the system can identify orientation of an anatomical feature of interest and further determine a position for the probe that will result in a better or optimal image of the feature. The transducer probe can be moved mechanically with a robotic arm from a first position to a second position in a variety of ways. In some aspects, images (e.g., 2D and/or 3D images) can be acquired at selected or predetermined time intervals during the movement from the first position to the second position. With this option, algorithms can be used at some or all of the time intervals to identify where the probe is positioned in relation to the anatomical feature of interest. In certain aspects, the probe may move in one movement from the first position to the second position, and further optimized after be moved to the second position using algorithms to optimize the position and/or orientation of the probe to provide the best image of the anatomical feature.

As referred to herein, the ultrasound systems of the present invention can include image algorithm and/or processing methods that are trained to determine orientation of anatomical features being imaged. The training algorithms can be stored on the system and accessed to identify orientation of features in acquired images. After an orientation is determined, the system can further move the transducer array so as to generate more optimal images in a new orientation that is calculated by the system. For example, the AMA 34 may receive scans from the scan converter 32 and rapidly segment a majority of fetal anatomy from 2D ultrasound scans or 3D volumes using a model-based approach, and in doing so, may determine quickly the orientation of the fetus and those areas where sufficient or insufficient image data was acquired. The AMA 34 may not require a template or image from another imaging modality to match the acquired image to perform its analysis. This may speed analysis time and avoid having the sonographer perform pre-alignment measurements. The fetal model may be based on articulated rigid body transformations defining a kinematic tree. The kinematic tree may define a fetal skeleton model. Another fetal modeling approach that may be used is a deformable template. For example, a fetal skull may be estimated as two overlapping spheres, which are modified by modeling parameters to fit the acquired volume to determine the fetal skull orientation. Additional fetal modeling approaches may also be used. The different fetal models may be used exclusively or in combination. For example, a kinematic tree model may be used to find the orientation of the fetus and skeletal structure, and then a different anatomical model is applied to locate and differentiate internal organs of the fetus such as the heart, brain, and spinal cord. The sonographer may choose which fetal model or models to use. In other embodiments, the AMA 34 may automatically apply a given model. The AMA 34 may also apply various models or combination of models until a best fit for fetal orientation is determined.

In some embodiments, the ultrasound systems of the present invention can be configured to identify whether a sufficient portion of anatomical feature is present in an acquired image. If more of the anatomical feature can be imaged, then the system will identify the insufficiency and reorient to ultrasound beam to include more of the feature for optimal imaging. In one embodiment, a sufficient image may be an image containing an entire key anatomical view. For example, an image of the fetal skull would be insufficient if a portion of the cranium was not in the image. Optionally, a sonographer may be allowed to override this sufficiency determination if a circumstance did not require an entire key anatomical view or a non-standard view was desired. The sufficient image may further be of an adequate resolution such that it would be useful for a reviewing physician for diagnostic purposes. An adequate resolution may also be defined as a certain desired number of lines per unit of measurement (e.g., centimeters, millimeters squared) in one or more dimensions. Alternatively, or in addition to the resolution, the AMA 34 may determine the image is sufficient if it was acquired in a scan plane aligned with the aperture of the transducer array of the ultrasound probe. Once the AMA 34 has determined the fetal orientation and the scan plane, the AMA 34 may calculate the required translation of the transducer array 10' from its current position to acquire a desired and/or improved image of a key anatomical view. The AMA 34 may instruct the motor controller to translate the transducer array 10' such that the aperture is positioned to acquire the desired image in a scan plane aligned with the aperture.

In yet another embodiment, a sonographer may begin a fetal exam by placing the probe on the abdomen of a subject. The sonographer may or may not use the user control panel 38 to indicate which key anatomical view of the fetus is being sought. The sonographer may manually move the ultrasound probe across the abdomen until a desired view is achieved. The sonographer may then acquire an image. The AMA 34 may receive the acquired image or volume from the scan converter 32 and analyze the image to determine its resolution and/or the completeness of the anatomical view. The AMA 34 may determine the imaging plane and orientation of the fetus. The AMA 34 may have received input from the user control panel 38 as to which anatomical view the sonographer is currently attempting to acquire. However, in some embodiments, the AMA 34 may be able to process the acquired image or volume and automatically determine which anatomical view is desired by the sonographer. If the AMA 34 determines a complete key anatomical view of sufficient resolution has been acquired, the AMA 34 may send a signal to the graphics processor 36 to provide a visual indication on the display 40 to alert the sonographer that the key anatomical view has been acquired successfully. The sonographer may confirm and save the image to a storage medium (not shown in FIG. 1) accessible to the imaging system. The sonographer may end the fetal exam or attempt to acquire an additional key anatomical view. In some embodiments, the AMA 34 may automatically save the successfully acquired anatomical view and begin attempting to acquire the next standard anatomical view or end the exam. In some embodiments, the imaging system may also continuously acquire images for analysis by the AMA 34. The AMA 34 may track fetal movements during the imaging exams and adjust the position of the aperture based, at least in part, on the fetal movements. This may assist the sonographer in maintaining the current view being acquired and/or observed.

In certain embodiments, if the AMA 34 determines that the image resolution is poor and/or the key anatomical view is incomplete because it is outside the field of view, the AMA 34 may then calculate a position of the aperture of the transducer array 10' that may provide a more complete and/or higher resolution image of the desired anatomical view by acquiring the key anatomical view with a scan plane of the aperture. The AMA 34 may send instructions to the motor controller, and the motor controller may operate the motor or motors in the ultrasound probe to move the transducer array 10' to the desired location. The imaging system may then acquire a new image for analysis by the AMA 34. If the image is determined to be sufficient, the image may be provided to the sonographer on the display 40 along with an indication that the key anatomical view has been acquired successfully. Similar to above, the sonographer may confirm and save the image. In some embodiments, the imaging system may acquire multiple images and provide one or more of the images to the sonographer on the display 40. The sonographer may review the images and choose which image to save. The sonographer may also be able to decline all of the provided images and choose to re-attempt to acquire the desired anatomical view.

If the AMA 34 determines a desired location of the aperture cannot be achieved by translating the transducer array 10' within the probe, the AMA 34 may send a signal to the graphics processor 36 to alert the sonographer on the display 40 that the sonographer may need to move the probe to a new location on the subject's abdomen. In some embodiments, the AMA 34 may provide visual instructions on the display 40 to the sonographer of how to reposition the probe. Once the probe is repositioned by the sonographer, the sonographer may then acquire a new image for analysis by the AMA 34.

It is noted that the systems and methods of the present invention can be applied to imaging a variety of anatomical features. For example, AMA 34 is capable of modeling other anatomy of interest, such as a heart using known modeling algorithms. An example of a non-fetal anatomical model is described in PCT/IB2011/053710, "Automated three dimensional aortic root measurement and modeling." Other anatomical models may be used. In non-medical applications, the anatomical model may be replaced with any appropriate model for the object to be imaged for determining orientation and areas where sufficient or insufficient image data are found.

Figure 4:
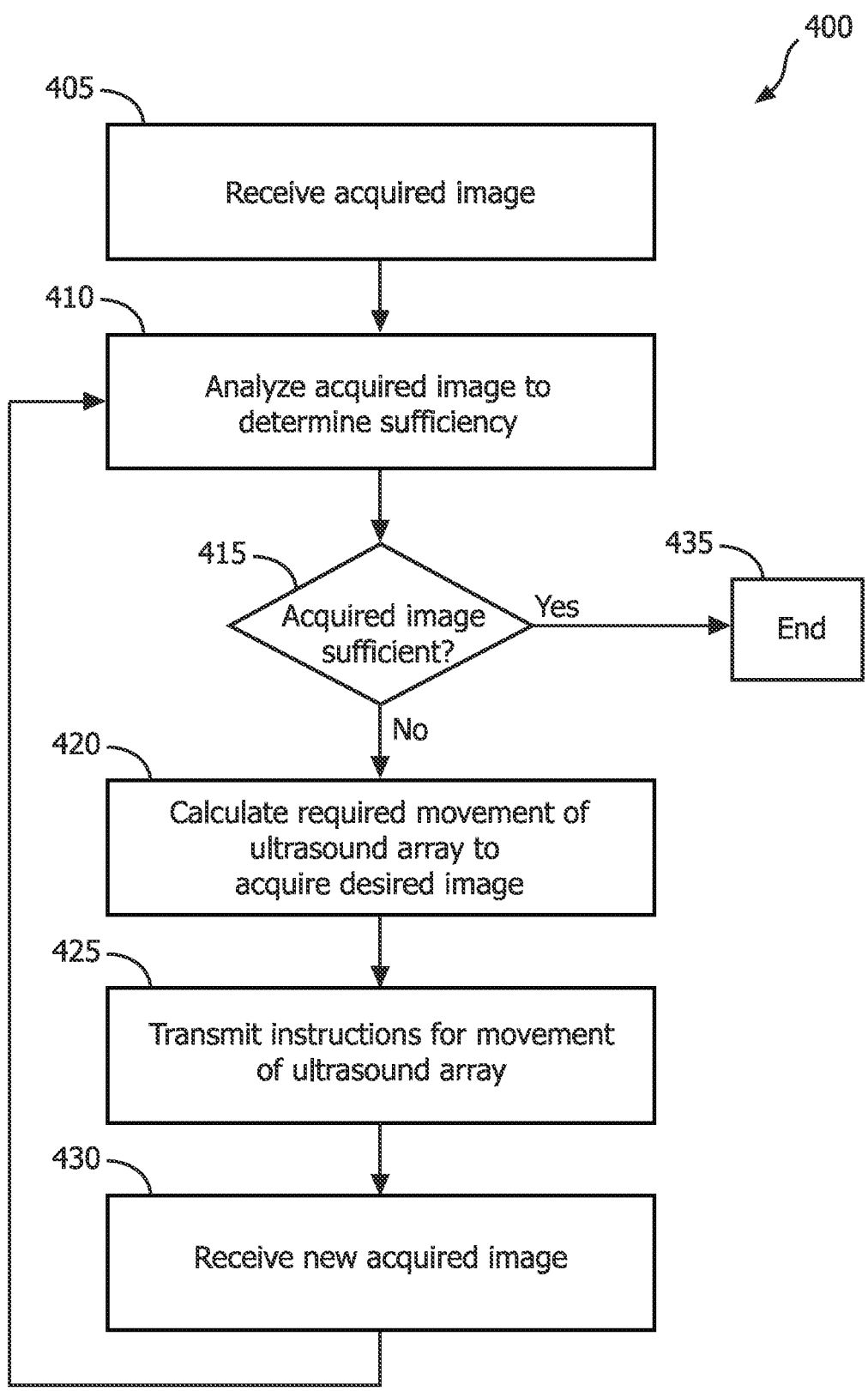
FIG. 4 is a flow chart of an operation of an illustrative embodiment of the invention.

A variety of methods can be used to operate the systems and probes of the present invention to function anatomically intelligently. For example, a flow chart 400 of a method according to an embodiment of the invention that is performed by the AMA 34 in the above procedures is shown in FIG. 4. The AMA 34 first receives an acquired image at Step 405. The AMA 34 analyzes the image to determine if it is sufficient at Step 410. The anatomical view, e.g., may be complete and/or the image may be of adequate resolution. In an alternative embodiment, regardless of the resolution of the image, the image may be determined to be insufficient if it was determined by the AMA 34 to have been acquired in a scan plane that is not aligned with the aperture of the transducer array 10'. If the acquired image is sufficient at Step 415, the process ends at Step 435. Optionally, the AMA 34 may transmit instructions to the graphics processor 36 to alert the sonographer to the sufficiency of the image and/or automatically save the acquired image to a storage medium accessible to the imaging system. If the acquired image is determined to not be sufficient at Step 415, at Step 420 the AMA 34 calculates the required movement of the ultrasound transducer array 10' to position the aperture such that a higher resolution and/or complete anatomical view may be acquired. The position of the aperture may correspond to a location wherein the complete anatomical view may be acquired in a scan plane of the aperture of the transducer array 10'. The AMA 34 then transmits instructions for moving the ultrasound transducer array 10' to motor controller at Step 425. Alternately, the AMA 34 may transmit instructions to the transmit control 18 to position the aperture via beamforming. At Step 425, the AMA 34 may transmit instructions to both the transmit control 18 and the motor controller. Once the aperture has been positioned to the new location, at Step 430 the AMA 34 may receive a new acquired image for analysis. The process then returns to Step 410 where the AMA 34 analyzes the new acquired image. Optionally, if the aperture location calculated by the AMA 34 cannot be achieved by beamforming or motor translation of the transducer array 10', the AMA 34 may send instructions to the graphics processor 36 to visually alert the sonographer that the position of the probe may need to be moved. As discussed above, the AMA 34 may provide instructions to the sonographer for moving the probe to a new location. In other embodiments, the AMA 34 may send instructions to move the aperture as close to the calculated position as possible. The AMA 34 may then analyze a new image acquired by the ultrasound probe, and only if this image is also insufficient, send instructions to notify the sonographer.

Although the system is described as providing visual instructions to the sonographer on the display 40, other methods of providing instructions or information to the sonographer may be used. For example, an audio indication such as a beep or a recorded voice may be provided to the sonographer via speakers (not shown in FIG. 1) included in the imaging system. A combination of audio and visual signals may also be used.

In some embodiments, the probe may be operated remotely by a sonographer with a robotic arm. In these embodiments, the AMA 34 may provide instructions to additional motor controllers that may operate the robotic arm to move the probe to the desired position. Such embodiments may be used during fetal exams but may be desirable in applications where the safety of the sonographer may be compromised. Procedures where x-ray imaging is being performed concurrently with ultrasound imaging or in certain non-medical imaging applications where industrial hazards exist may make remote navigation of the ultrasound probe desirable.

In various embodiments where the above-described systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system has been described with reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, muskuloskeletal, splenic, cardiac, arterial and vascular systems, as well as other imaging applications related to ultrasound-guided interventions. Further, the present system may also include one or more programs which may be used with conventional imaging systems so that they may provide features and advantages of the present system.

Further, the present systems, apparatuses, and methods, may also be extended to any small parts imaging where the clear landmarks can be defined and reproduced. Further, the present methods may be embedded in a program code which may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging. Further, analysis techniques such as, for example, QLAB™ may be available on-cart with an imaging apparatus or as a post-processing program which may be run outside of an examination room. Further, multiple nodules, anatomical entities such as follicles, or other detectible objects, may be marked using the present system. Further, the method of the present systems may be applied to volumes acquired using transducers such as, for example, 2D array transducers, which may include, for example, X-matrix™ or mechanical transducers.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A medical imaging system comprising code stored on a non-transitory computer readable medium, which when executed by a processor, causes the system to:
   acquire a first ultrasound image of at least one anatomical feature;
   segment the acquired first ultrasound image of the at least one anatomical feature;
   determine an orientation of the at least one anatomical feature within the first ultrasound image;
   determine, by a trained analyzer, the orientation of the at least one anatomical feature within the first ultrasound image to be sufficient or insufficient without requiring a template or an image from another imaging modality;
   calculate a position for an ultrasound acoustic aperture to obtain a second ultrasound image of the at least one anatomical feature in response to a determination by the trained analyzer of the orientation of the at least one anatomical feature within the first ultrasound image to be insufficient; and
   move the ultrasound acoustic aperture to the position to acquire the second ultrasound image.

2. The medical imaging system of claim 1, wherein the code further causes the system to:
   alert a user if the ultrasound acoustic aperture cannot be moved to the position.

3. The medical imaging system of claim 1, wherein the code further causes the system to:
   acquire the second ultrasound image using the ultrasound acoustic aperture at the position;
   determine an orientation of the at least one anatomical feature within the second ultrasound image; and
   determine, by the trained analyzer, the orientation of the at least one anatomical feature within the second ultrasound image to be sufficient or insufficient.

4. The medical imaging system of claim 3, wherein the code further causes the system to:
   alert a user to at least one of:
      a determination by the trained analyzer of the orientation of the at least one anatomical feature within the first ultrasound image as sufficient or insufficient, and
      a determination by the trained analyzer of the orientation of the at least one anatomical feature within the second ultrasound image as sufficient or insufficient.

5. The medical imaging system of claim 1, wherein the ultrasound acoustic aperture is moved by moving an ultrasound transducer probe including the ultrasound acoustic aperture to the position.

6. The medical imaging system of claim 1, wherein the ultrasound acoustic aperture is moved by translating an ultrasound transducer probe that is configured to move the ultrasound acoustic aperture in at least two degrees of freedom.

7. The medical imaging system of claim 1, wherein the ultrasound acoustic aperture is moved by beamforming an ultrasound transducer array defining the ultrasound acoustic aperture.

8. The medical imaging system of claim 1, wherein an image plane and the orientation of the at least one anatomical feature within the first ultrasound image are determined at least in part by an articulated rigid body transformation model.

9. The medical imaging system of claim 1, wherein an image plane and the orientation of the at least one anatomical feature within the first ultrasound image are determined at least in part by a deformable template model.

10. The medical imaging system of claim 1, wherein a determination by the trained analyzer of the orientation of the at least one anatomical feature within the first ultrasound image is determined, at least in part, by a resolution of the first ultrasound image.

11. The medical imaging system of claim 1, wherein a determination by the trained analyzer of the orientation of the at least one anatomical feature within the first ultrasound image is determined, at least in part, by the first ultrasound image containing an entire key anatomical view.

12. The medical imaging system of claim 1, wherein a determination by the trained analyzer of the orientation of the at least one anatomical feature within the first ultrasound image is determined, at least in part, by the first ultrasound image being acquired in a scan plane of the ultrasound acoustic aperture.

13. The medical imaging system of claim 1, wherein the first and second ultrasound images comprise 2D or 3D ultrasound images, respectively.

14. The medical imaging system of claim 1, wherein the code further causes the system to acquire more than one ultrasound image while moving to the position.

15. The medical imaging system of claim 1, wherein the other imaging modality comprises a stored image.

16. A method, comprising:
    receiving an acquired ultrasound image of at least one anatomical feature at a medical imaging system;
    segmenting the acquired ultrasound image of the at least one anatomical feature;
    analyzing an orientation of the at least one anatomical feature within the acquired ultrasound image with a processor of the medical imaging system;
    calculating, with the processor, a position of an ultrasound acoustic aperture to acquire a desired orientation of the at least one anatomical feature within a scan plane of the ultrasound acoustic aperture in response to an undesired orientation of the at least one anatomical feature within the acquired ultrasound image without requiring a template or an image from another imaging modality;
    calculating, with the processor, a movement of an ultrasound array to move the ultrasound acoustic aperture to the position; and
    transmitting instructions from the processor to a controller to move the aperture to the position.

17. The method of claim 16, further comprising receiving a new acquired ultrasound image of the at least one anatomical feature at the medical imaging system.

18. The method of claim 16, wherein the instructions are instructions for a motor.

19. The method of claim 16, wherein the instructions are instructions for beamforming with an ultrasound transducer.

20. The method of claim 16, wherein the analyzing the acquired ultrasound image includes fitting the acquired ultrasound image of the at least one anatomical feature to an anatomical model to determine an imaging plane and an orientation of the acquired ultrasound image.

21. The method of claim 16, wherein analyzing the acquired ultrasound image of the at least one anatomical feature includes determining a resolution of the acquired ultrasound image.

22. The method of claim 16, wherein the other imaging modality comprises a stored image.

* * * * *